US006902712B2

United States Patent
Davis

(10) Patent No.: US 6,902,712 B2
(45) Date of Patent: *Jun. 7, 2005

(54) ABSORBENT LINER FOR STERILIZATION PROCESS AND METHOD OF STERILIZING SURGICAL INSTRUMENTS

(75) Inventor: Phillip Davis, Weston, CT (US)

(73) Assignee: General Hospital Supply Corporation, Wilton, CT (US)

( * ) Notice: Subject to any disclaimer, the term of this patent is extended or adjusted under 35 U.S.C. 154(b) by 87 days.

This patent is subject to a terminal disclaimer.

(21) Appl. No.: 10/012,663

(22) Filed: Oct. 30, 2001

(65) Prior Publication Data

US 2002/0064478 A1 May 30, 2002

Related U.S. Application Data

(63) Continuation-in-part of application No. 09/686,453, filed on Oct. 11, 2000.
(60) Provisional application No. 60/158,779, filed on Oct. 12, 1999.

(51) Int. Cl.⁷ .............................. A61L 2/20; A61L 2/26
(52) U.S. Cl. ........................ 422/300; 422/297; 206/523
(58) Field of Search .................. 422/297, 300; 208/523, 557; 521/170, 174

(56) References Cited

U.S. PATENT DOCUMENTS

| | | |
|---|---|---|
| 3,566,871 A | 3/1971 | Richter et al. |
| 3,814,101 A | 6/1974 | Kozak |
| 4,023,570 A | 5/1977 | Chinai et al. |
| 5,009,653 A | 4/1991 | Osborn, III |
| 5,104,909 A * | 4/1992 | Grasel et al. ................ 521/159 |
| 5,635,134 A | 6/1997 | Bourn et al. |
| 6,440,375 B1 * | 8/2002 | Davis et al. ................ 422/300 |

FOREIGN PATENT DOCUMENTS

JP 2001354275 A * 12/2001

OTHER PUBLICATIONS

General Hospital Supply Corporation. Product sheet for Instrument Tray Liner, Sep. 1997.*
*Absorbent Tray Liner,* Kimberly–Clark Corporation, 1996.
*Absorbent Tray Liner,* Graphic Controls Corporation, 1996.

* cited by examiner

*Primary Examiner*—E. Leigh McKane
(74) *Attorney, Agent, or Firm*—St. Onge Steward Johnston & Reens LLC

(57) ABSTRACT

The present invention is directed to an absorbent liner for use in a sterilization process and, more particularly, to an absorbent liner for cushioning surgical instruments and sterilization packs and providing an advantageous moisture absorption functionality during and after completion of a sterilization process. The absorbent liner functions advantageously with steam or ethylene oxide gas as the sterilization agent. The absorbent liner is fabricated from a material having a desired level of moisture absorption, e.g., on the order of at least about thirty percent (30%) by dry weight, and is preferably fabricated from a hydrophilic polymeric foam material, e.g., a hydrophilic polyurethane foam. The disclosed absorbent liner may be advantageously utilized in sterilizing surgical instruments and in conjunction with sterilization carts such that potential residual moisture is eliminated from the surface of the sterilized surgical instruments and the shelves of the sterilization carts.

14 Claims, 2 Drawing Sheets

ABSORBENT LINER FOR STERILIZATION PROCESS AND METHOD OF STERILIZING SURGICAL INSTRUMENTS

CROSS-REFERENCE TO RELATED APPLICATIONS

This application is a continuation-in-part application of U.S. patent application Ser. No. 09/686,453, filed Oct. 11, 2000 which claims benefit of U.S. Provisional Patent Application Ser. No. 60/158,779, filed Oct. 12, 1999, the contents of each of which are incorporated herein by reference.

BACKGROUND

1. Technical Field

The present invention relates to liners such as trayliners and shelf-liners for use in a sterilization process and, more particularly, to an absorbent liner for cushioning surgical instruments and sterilization packs and providing an advantageous moisture absorption functionality during and after completion of a sterilization process. In a preferred embodiment of the present invention, an absorbent, foam plastic absorbent liner is disclosed for cushioning surgical instruments and sterilization packs and providing an advantageous moisture absorption functionality during and after sterilization procedures that utilize steam and/or ethylene oxide gas as a sterilization agent.

2. Background of the Related Art

As is well known, surgical instruments used in the healthcare industry must be sterilized before and after each use. Sterilization, of course, frees instruments from microorganism contamination, to prevent infections and the spread of diseases among patients. All medical procedures rely upon a stringent program of sterilization.

The medical device industry has addressed the sterilization requirements in the surgical field by offering two general types of surgical instruments: reusable instruments and single use, or disposable instruments. Reusable instruments are typically composed of stainless steel and are typically sterilized before their initial use and then cleaned and resterilized prior to each subsequent use thereof. Single use or disposable instruments, on the other hand, are often fabricated primarily from plastic materials, thereby reducing costs associated with manufacture, and are discarded after use in a single procedure.

With respect to reusable surgical instruments, e.g., forceps, graspers, dissectors, probes, hemostats, scissors and the like, historically sterilization and resterilization have been accomplished using two primary sterilization modalities: steam sterilization and ethylene oxide sterilization. Of the two primary sterilization modalities, steam sterilization has been the overwhelmingly dominant method of sterilization in the surgical instrument field. In a broad sense, the sterilization process generally involves placing instruments to be sterilized in a tray, wrapping the instruments and the tray with a sterilization wrap, and placing the wrapped tray and instruments in a sterilization chamber where the instruments are exposed to the sterilization medium of either steam or ethylene oxide. Preferably, the instruments are placed in a tray and wrapped before initiating exposure to the sterilization medium. Wrapping the tray generally contributes to providing a level of protection to the surgical instruments, e.g., during post-sterilization storage and handling prior to actual use, and to maintaining the instruments in a dry, sterile condition. Typically, sterilization trays are wrapped with a sterilization wrap, e.g., paper. Other instruments to be sterilized include basins. Basins are separated by cotton towels or other absorbent materials and then wrapped in sterilization wrap prior to sterilization.

One long and continuing problem encountered with steam and/or ethylene oxide sterilization, however, is the presence of moisture that remains on the implements such as on sterilized instruments, i.e., within the sterile wrap, at the conclusion of the sterilization process. This residual moisture can range from slight levels of dampness to visible droplets on the surface of surgical instruments. Such residual moisture is both undesirable and is unacceptable because such moisture could permit migration of surface microorganisms, thereby penetrating the wrapped tray or basin and rendering its contents contaminated.

A wrapped tray or basin with residual moisture has been termed a "wet pack," i.e., a wrapped tray containing surgical instruments having surface moisture on the inside and/or outside of the wrapped tray, e.g., during and after the sterilization process. In one of its marketing publications, Getinge/Castle, Inc. of Rochester, N.Y., a major manufacturer of sterilizers, refers to the "wet pack" problem as "an age old predicament." Wet pack problems may be caused and/or exacerbated by, e.g., the use of new sterilizers, boiler or plumbing changes or even ambient humidity variations due to air conditioning, etc.

Another problem arises when the wrapped trays and basins are loaded on sterilization carts having multiple shelves and rails and which are then wheeled into a sterilizer where the wrapped trays are sterilized along with the cart. In such a case, condensation may drip from a shelf or a rail onto the wrapped tray causing a wet pack. Also, the wrapped tray or basin may become stained during sterilization or even torn during loading or removal from a sterilization cart because of the condition of the sterilization cart. That is because during repeated use, the sterilization carts may begin to oxidize and degrade exposing sharp edges.

In some cases, shelves of sterilization carts may be laboriously wrapped with absorbent wrappers or thermal blankets that then must be adhered to the shelves. In a further step, the edges of the absorbent wrappers or thermal blankets must also be bound to prevent fraying and shedding of the wrappers or blankets and subsequent passage thereof into the sterilization medium. Since the absorbent wrappers and thermal blankets require a large amount of labor to replace, the sterilization carts generally undergo an excessively high number of sterilization cycles in the sterilizer before they are replaced. This allows for the buildup of undesirable materials and microorganisms within the absorbent wrappers and thermal blankets.

What is needed, therefore, is a more effective means than, e.g., a paper or cotton product for preventing wet packs, degradation of sterilization carts, the labor intensive replacement of shelf-liners and the resulting potential for contamination of sterilized surgical instruments.

SUMMARY OF THE DISCLOSURE

According to the present invention, a highly absorbent liner is provided that may be advantageously placed, in one embodiment as a trayliner, in a sterilization tray, e.g., along the tray bottom, or, in another embodiment as a shelf-liner, on a shelf of a sterilization cart to absorb potential residual moisture generated during the sterilization process. The highly absorbent liner advantageously maintains surgical instruments positioned in a wrapped tray or the shelves of the sterilization cart itself in a "dry" condition at the completion of the sterilization process and further cushions the instrumentation, thereby minimizing the potential for instrument damage during post-sterilization handling. Also, the shelf-liners cushion sterilization packs, such as wrapped trays or basins, which may be loaded onto shelves of the sterilization carts and thereby prevent damage, stains or the like to the packs. The highly absorbent liner of the present invention is preferably compatible with a steam or ethylene oxide sterilization process.

In addition, the liners of the present invention advantageously neither interfere with nor inhibit conventional steam and ethylene oxide sterilization procedures. Thus, the absorbent liners of the present invention permits air removal, sterilant penetration/evacuation, drying and effective aeration of instruments that are sterilized according to conventional steam or ethylene oxide sterilization procedures. Moreover, the absorbent liners of the present invention are advantageously lint-free, preferably pre-cut to fit standard sterilization trays or other surgical instruments and variously sized sterilization carts, and relatively inexpensive such that disposal of the liner after a single use or limited number of uses is cost effective.

The absorbent sterilization liner may be advantageously utilized in a sterilization method to achieve superior results, particularly in terms of reduced residual moisture on the surface(s) of surgical instrument(s) or sterilization carts. A sterilization method according to the present invention generally includes placing a shelf-liner on a shelf of a sterilization cart, placing one or more sterilization packs on top of the shelf-liner, and then sterilizing the sterilization cart and sterilization packs with steam or ethylene oxide.

In a preferred embodiment of the present invention, an absorbent liner is fabricated from a material that is moisture absorbent, i.e., hydrophilic, and preferably a material that absorbs moisture up to about thirty percent (30%) of its weight. Absorbent liners fabricated from materials having moisture absorbency at a level as described herein have been found to achieve beneficial results, e.g., prevent residual moisture on instrument surfaces post-sterilization, and allow effective operation of conventional steam and ethylene oxide processes. A preferred material for use in fabricating an absorbent liner according to the present invention is a hydrophilic polyurethane foam available from Foamex International, Inc. (Linwood, Pa.) under the tradename Aquazone®.

In sum, an absorbent liner and a method of sterilization according to the present invention, have been found to reduce "wet pack" problems associated with the sterilization of surgical instruments. Still other features and advantages of the presently disclosed absorbent sterilization liner and method for sterilizing surgical instruments will become apparent upon reading the following detailed description in conjunction with the attached drawings.

BRIEF DESCRIPTION OF THE DRAWINGS

So that those having ordinary skill in the art to which the disclosed trayliner and associated method appertains will more readily understand how to employ and use the same, reference may be had to the drawings wherein.

DETAILED DESCRIPTION OF PREFERRED EMBODIMENT(S)

Figure 1:
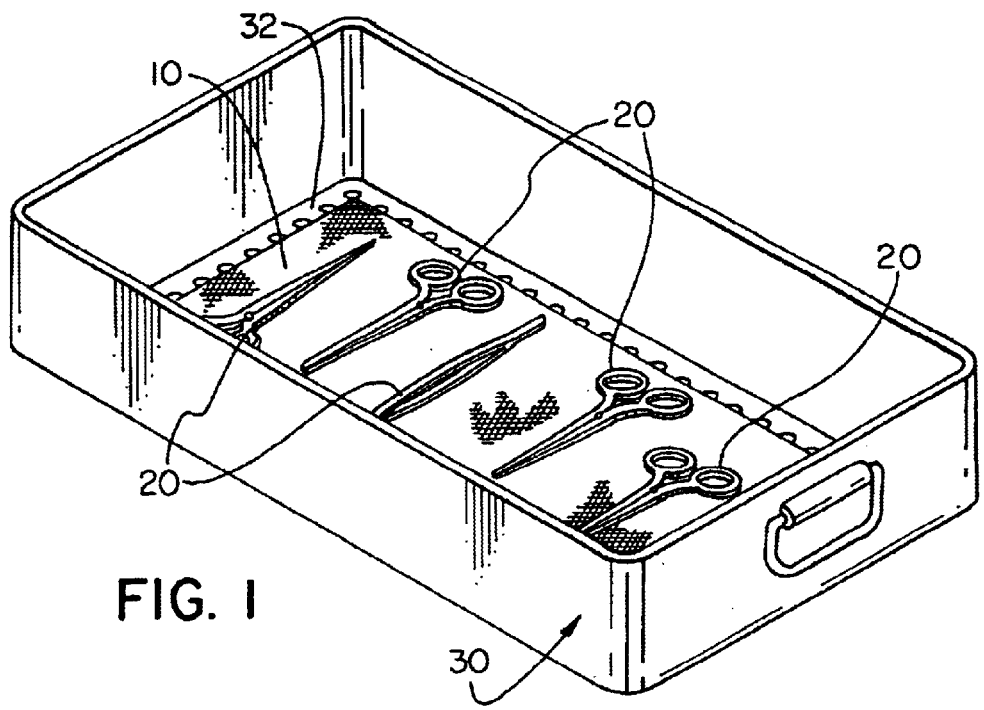
FIG. 1 is a perspective view of a trayliner according to the present invention, lying beneath surgical instruments within a sterilization tray.
Figure 2:
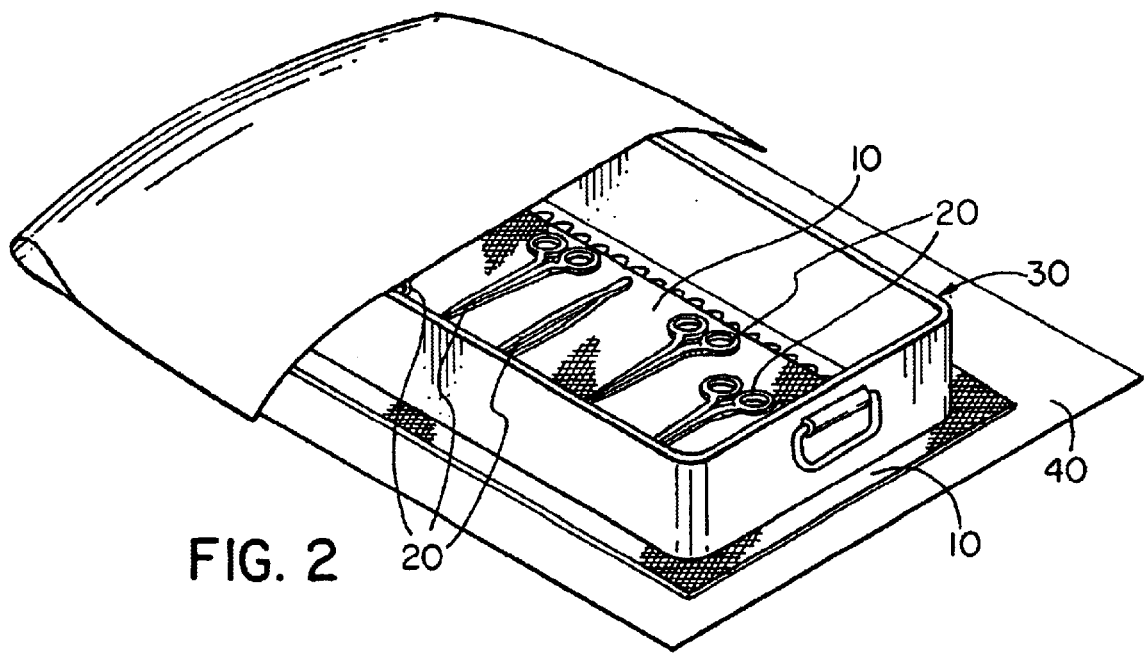
FIG. 2 is a perspective view of an alternative trayliner embodiment according to the present invention, positioned under the sterilization tray of FIG. 1, with a sterilization wrap positioned therearound.

Referring to FIGS. 1 and 2, a first embodiment of an absorbent liner in accordance with the present invention is illustrated. In particular, an absorbent trayliner 10 is provided for introduction into a sterilizing system in connection with the sterilization process. The absorbent trayliner 10 of the present embodiment advantageously functions to prevent the presence of residual moisture on the surface of surgical instruments at the conclusion of the sterilization process by absorbing such potential residual moisture. The absorbent trayliner 10 of the present invention further advantageously cushions surgical instruments to be sterilized, e.g., forceps, graspers, dissectors, probes, hemostats, scissors and the like, both during and after a sterilization process. Trayliner 10 is preferably fabricated from a hydrophilic polyurethane foam that absorbs on the order of thirty percent (30%) by dry weight and is adapted for use in sterilization processes that utilize steam or ethylene oxide as the sterilizing agent. A particularly preferred material for use in fabricating absorbent trayliner 10 is Aquazone® polyurethane foam.

With reference to FIG. 1, absorbent trayliner 10 generally comprises a sheet of absorbent material cut to substantially cover a base 32 of a sterilization tray 30. The base 32 of the sterilization tray 30 may be solid or perforated, as is known in the art. As shown absorbent trayliner 10 is of rectangular configuration; however, alternative geometries are contemplated, e.g., as may be appropriate for specific sterilization tray configurations. Absorbent trayliners may be dimensioned depending upon the application. Preferred absorbent trayliners 10 measure approximately 12×12, 12×14, 12×16, 12×18, 12×20 and 12×22 inches, respectively, and are approximately ⅛th inch in thickness. Trayliners 10 preferred for use in separating basins measure approximately 3×24 inches and may also be ⅛ inch in thickness.

Preferably, the absorbent trayliner 10 is fabricated from a non-woven, lint free material that is compatible with both steam and ethylene oxide sterilization. The absorbent trayliner 10 preferably is fabricated from a hydrophilic polymeric foam plastic, e.g., a hydrophilic polyurethane foam. The absorbent trayliner 10 preferably absorbs on the order of at least about thirty percent (30%) by dry weight. A specific foam plastic suitable for use is a non-reticulated polyurethane ester foam available from Foamex Corporation (www.foamex.com) under the tradename Aquazone® foam. The Aquazone® foam absorbs moisture of approximately thirty three percent (33%) by dry weight.

Typical physical properties of the Aquazone® foam include the following:

| | |
|---|---|
| Foam type: | Polyurethane Ester Foam |
| Reticulation: | None |
| Pore Size (ppi): | 85 |
| Density (lbs/ft$^3$): | 1.8 |
| Wet tensile (psi): | 25 |
| Dry tensile (psi): | 30 |
| Dry tear (pli): | 4.2 |
| Wet elongation (%): | 480 |

-continued

| | |
|---|---|
| Dry elongation (%): | 400 |
| 25% CFD (psi): | 0.56 |
| 65% CFD (psi): | 0.81 |
| 58% Compression Set (%): | 11 |
| Water-holding (% dry weight): | 33 |
| Wet-out (sec): | <10 |
| Volume swell (%): | 3 |
| 2 min H₂O capillary height (cm): | 2.5 |

The absorbent trayliner 10 of the present invention is particularly adapted for use in a steam sterilization system or ethylene oxide sterilization system. As is known, a sterilization system generally includes a sterilization chamber that is adapted to receive instruments to be sterilized, and a source of a sterilizing agent, e.g., steam or ethylene oxide, connected to the sterilization chamber.

A preferred method for sterilizing surgical instruments 20 according to the present invention includes positioning the trayliner 10 in the base of the tray 30, as shown in FIGS. 1 and 2, and positioning instruments 20 on the trayliner. The types of instruments 20 that may benefit from the sterilization method disclosed herein includes all conventional surgical instruments, particularly reusable surgical instruments composed of stainless steel. Determinations as to the types of surgical instruments 20 to be placed on tray 30, the numbers/weights of such surgical instruments, the spacing of such surgical instruments, sterilization cycles, and the like, are made according to conventional sterilization criteria. Although not, shown, a trayliner 10 could also be placed on top of the instruments to provide further absorption capabilities to the system, as will be apparent to persons skilled in the art.

As shown in the alternative embodiment of FIG. 2, tray 30 contains absorbent trayliner 10 and a plurality of instruments 20 positioned thereon. Tray 30 is then advantageously wrapped in a conventional sterilization wrap 40. Sterilization wrap 40 may be fabricated from paper and, optionally, a second absorbent trayliner 10 or other cushioning member may be placed between tray 30 and sterilization wrap, thereby reducing the risk that wrap 40 may be torn by the corners of tray 30. Once wrapped in the sterilization wrap 40, tray 30 is ready to be placed in a sterilization unit for sterilization of surgical instruments 20. At the conclusion of the sterilization cycle, tray 30 is typically removed from the sterilization unit (not pictured), and the sterilized instruments 20 are, in due course, removed from the tray and made ready for subsequent surgical procedures. At the conclusion of the sterilization cycle, the absorbent trayliner 10 of the present invention is typically disposed of in a conventional waste container.

The absorbent trayliner of the present invention provides significant benefits to the reliability and efficacy of conventional sterilization operations. Ideally, as is known in the art, when the sterilization system is operating at peak performance a sterilization system that utilizes steam or ethylene oxide as the sterilizing agent will be totally dry at the conclusion of the sterilization cycle. However, as discussed above due to ambient humidity, plumbing, etc., sterilization systems are highly variable in operation and such systems do not always operate at peak levels. As a result, without use of an absorbent trayliner 10, it is not uncommon for residual moisture to be found on the surface of sterilized instruments at the conclusion of the sterilization cycle. The absorbent trayliner of the present invention exhibits sufficient hydrophilicity to absorb an amount of moisture sufficient to address typical operative variability.

Trayliners according to an embodiment of the present invention have been tested to ascertain their effectiveness in absorbing moisture, i.e., removing any potential residual moisture from the surface of sterilized instruments. Results of a water capacity test on a polyurethane foam in accordance with the present invention along with those of a cotton towel and a liner manufactured by the Kimberly-Clark Corporation of Neenah, Wis. are provided in TABLES 1–3. It will be recognized that such a test for water capacity may be found in the text entitled "Design and Applications of Hydrophilic Polyurethanes", by T. Thomson, Technomic Publishing Company, Inc., 2000, which is hereby incorporated herein by reference. These tests have verified the efficacy of the absorbent trayliners of the present invention.

TABLE 1

| LINER | | % WATER CAPACITY | % DRAINED WATER CAPACITY |
|---|---|---|---|
| Dry Weight | 14.22 g | | |
| Soaked Weight | 372.00 g | 2,616% | 1,460% |
| Drained Weight | 207.66 g | | |

TABLE 2

| COTTON TOWEL | | % WATER CAPACITY | % DRAINED WATER CAPACITY |
|---|---|---|---|
| Dry Weight | 96.10 g | | |
| Soaked Weight | 445.95 g | 464% | 302% |
| Drained Weight | 289.75 g | | |

TABLE 3

| K-C LINER | | % WATER CAPACITY | % DRAINED WATER CAPACITY |
|---|---|---|---|
| Dry Weight | 21.74 g | | |
| Soaked Weight | 222.41 g | 1,023% | 546% |
| Drained Weight | 118.71 g | | |

These results reveal that the water capacity of an absorbent tray liner of the present invention is significantly higher than that of a cotton towel. Accordingly, during the sterilization process, the tray liner 10 will absorb significantly more moisture that has condensed on surgical instruments than a cotton towel or a liner sold by the Kimberly-Clark Corporation will absorb.

Absorbent trayliners of the present invention along with cotton towels were also tested for moisture content after completion of the sterilization process to determine whether they had adequately dried during the drying cycle. The results showed that each of the inventive trayliners had completely dried. These results are provided in TABLE 4.

TABLE 4

| GRAVITY 132° C. | ABSORBENT INSTRUMENT TRAY LINER | | | COTTON TOWEL | | |
|---|---|---|---|---|---|---|
| | PRE WEIGHT | POST WEIGHT | MOISTURE RETENTION | PRE WEIGHT | POST WEIGHT | MOISTURE RETENTION |
| Run 1 | 12.67 g | 12.45 g | −1.77% | 99.77 g | 99.67 g | −0.10% |
| Run 2 | 12.85 g | 12.67 g | −1.42% | 103.68 g | 102.62 g | −1.03% |
| Run 3 | 12.83 g | 12.69 g | −1.10% | 100.22 g | 98.28 g | −1.97% |

The present invention, therefore, provides an absorbent trayliner 10 that functions to cushion surgical instruments in connection with the sterilization process, and further functions to absorb potential excess moisture that might remain on the surgical instruments at the conclusion of a steam or ethylene oxide sterilization process. The absorbent trayliner has been found to permit proper air removal, sterilant penetration/evacuation, and delivery of sterilized surgical instruments substantially devoid of residual moisture at the conclusion of a sterilization process. The absorbent trayliner has also been found to permit effective aeration of instruments sterilized with ethylene oxide.

Figure 3:
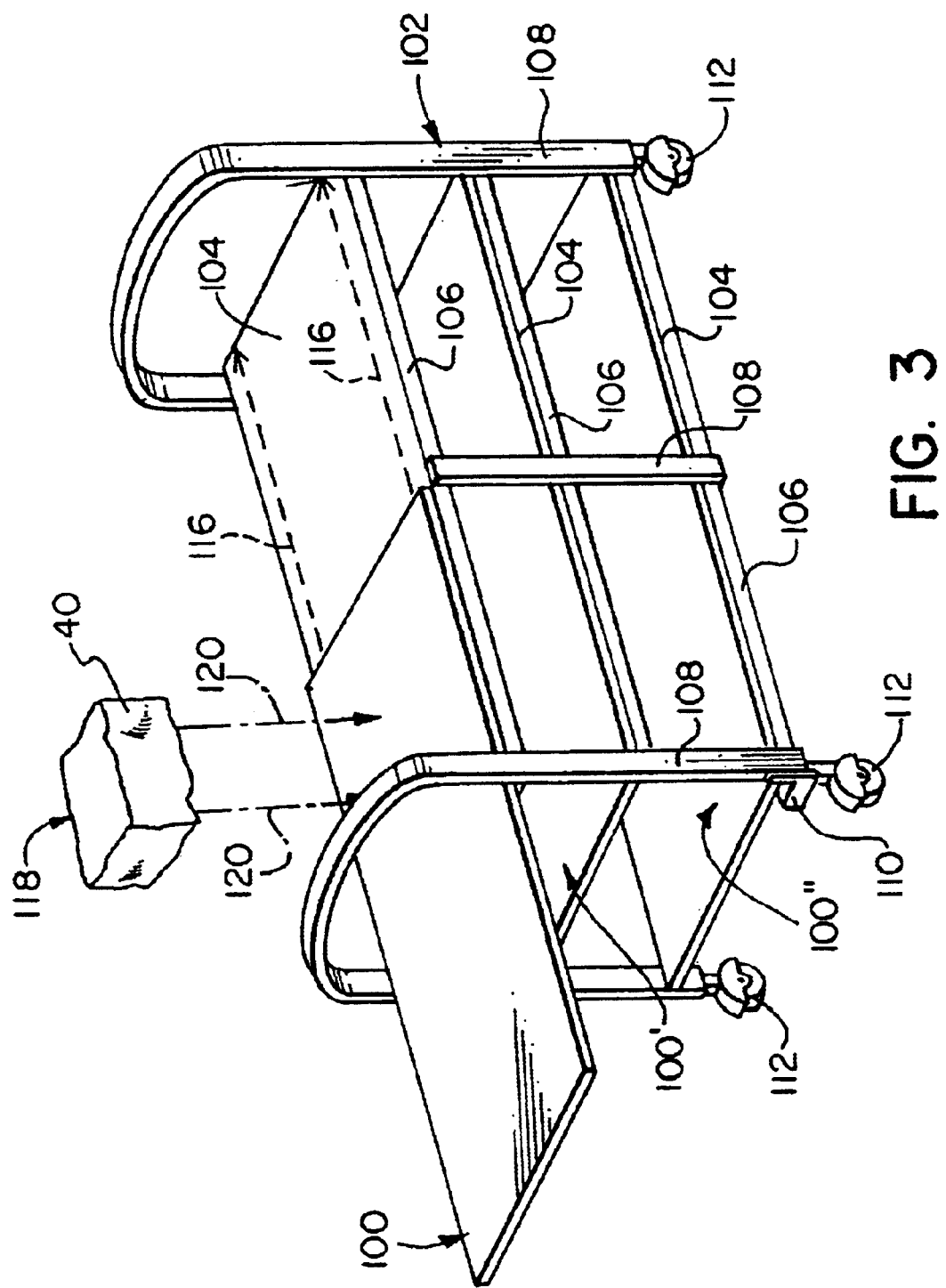
FIG. 3 is a perspective view of a sterilization cart including an unmounted, sterilization pack and two fully mounted shelf-liners and one partially mounted shelf-liner that are fabricated in accordance with another embodiment of the present invention.

Another embodiment of an absorbent liner in accordance with the present invention is illustrated in FIG. 3. In particular, shelf-liners 100, 100' and 100" are provided each of which is preferably composed of a polyurethane foam plastic material such as described above in connection with the trayliner 10. In addition, each of the shelf-liners 100, 100' and 100" are dimensioned for use with a sterilization carriage or cart such as that shown at 102. As shown, the sterilization cart 102 is generally composed of steel and includes sheet-like shelves 104 which are supported by horizontal beams 106 and vertical posts 108 having flanges 110. Casters 112 also may be provided for ease in movement of the sterilization cart 102. It will be appreciated that the sterilization cart 102 may be used in conjunction with, or loaded onto, other sterilization carts as is well known to the skilled artisan. One particular sterilization cart useful in the practice of the present invention is sold by the STERIS® corporation of Mentor, Ohio, under the mark AMSCO®.

The absorbent shelf-liners 100' and 100" are illustrated as being mounted on a shelf 104 and shelf-liner 100 is illustrated as being partially mounted requiring movement in the direction of arrows 114 for completing the mounting thereof. Once the absorbent shelf-liner 100 is mounted, the loading of, for example, a sterilization pack such as a wrapped tray 118 or a wrapped basin (not shown) may be carried out in the direction of arrows 120.

It will be appreciated that each of the absorbent shelf-liners 100, 100' and 100" may be dimensioned in accordance with the size of the sterilization cart. Preferred absorbent shelf-liners 100, 100' and 100" measure approximately 22×48 and 22×60 inches, respectively, and are approximately ¼th inch in thickness. Shelf-liners of such dimensions have been found in at least one instance to stand up to approximately 60 steam sterilization cycles before requiring replacement, e.g., in an Amsco Eagle Series #2053 Vacumatic sterilizer manufactured by the STERIS® corporation of Mentor, Ohio. However, it will be understood that overloading, otherwise improper loading of the sterilization cart or improper operation of the sterilizer may significantly reduce the number of sterilization cycles that the shelf-liner may withstand.

The shelf-liners 100, 100' and 100" advantageously absorb liquid while allowing the passage of the sterilization medium therethrough. Accordingly, the dripping of condensed sterilization medium from one shelf to another is significantly reduced along with oxidation of the sterilization cart due to repeated sterilization thereof.

The principles, preferred embodiments and modes of operation of the presently disclosed absorbent liners and methods of sterilizing surgical instruments have been described in the foregoing specification. The presently disclosed absorbent liners and methods of sterilization, however, are not to be construed as limited to the particular embodiments shown as these embodiments are regarded as illustrious rather than restrictive. Moreover, variations and changes may be made by those skilled in the art without departing from the spirit of the presently disclosed absorbent liners and methods of sterilization.

What is claimed is:

1. A sterilization system for sterilizing a surgical instrument comprising:
    a sterilizing agent for sterilizing the surgical instrument, said sterilizing agent re-siding on a surface of the surgical instrument as residual moisture after sterilization of the surgical instrument; and
    a sterilization liner for receiving the surgical instrument thereon, said sterilization liner dimensioned and configured to substantially cover a shelf of a sterilization cart in which it is positioned, said sterilization liner being fabricated from absorbent hydrophilic polymeric foam that absorbs the residual moisture from the surface of the surgical instrument after sterilization.

2. A sterilization system according to claim 1, wherein said sterilization liner is fabricated from a hydrophilic polyurethane foam.

3. A sterilization system according to claim 1, wherein said sterilization liner is fabricated from a hydrophilic polymeric foam that absorbs moisture of at least about thirty percent by dry weight.

4. A sterilization system according to claim 1, wherein said sterilization liner is fabricated from a hydrophilic polyurethane foam that is non-reticulated.

5. A sterilization system according to claim 1, wherein said sterilization liner is fabricated from a hydrophilic polyurethane foam that is capable of withstanding 60 cycles of steam sterilization.

6. A sterilization system according to claim 1, wherein said sterilization liner is approximately ¼ inch in thickness.

7. A sterilization system according to claim 1, wherein said sterilization liner is fabricated from a hydrophilic polymeric foam that has a water capacity of greater than approximately 1.023% by dry weight.

8. A sterilization system according to claim 7, wherein said sterilization liner is fabricated from a hydrophilic foam plastic that has a water capacity of approximately 2,616% by dry weight.

9. The sterilization system of claim 1, wherein said sterilization liner is approximately ⅛ inch in thickness.

10. A sterilization system comprising:

at least one sterilization pack;

a sterilizing agent for sterilizing said at least one sterilization pack, said sterilizing agent residing on a surface of the sterilization pack as residual moisture after the sterilization process; and a sterilization liner dimensioned and configured to substantially cover a shelf of a sterilization cart, said sterilization liner being fabricated from absorbent hydrophilic polymeric foam positioned to receive said sterilizing pack thereon for sterilizing by said sterilizing agent and for removing the residual moisture from said at least one sterliization pack after sterilization.

11. The sterilization system according to claim 10, wherein said sterilization liner is fabricated from a hydrophilic polyurethane foam.

12. The sterilization system according to claim 11, wherein the hydrophilic polyurethane foam is non-reticulated.

13. The sterilization system according to claim 10, wherein the hydrophilic polymeric foam absorbs moisture of at least about thirty percent by dry weight.

14. The sterilization system according to claim 10, wherein the hydrophilic polymeric foam is approximately ¼ inch in thickness.

* * * * *